United States Patent
Ducharme

(10) Patent No.: US 7,691,125 B2
(45) Date of Patent: Apr. 6, 2010

(54) SYSTEM AND METHOD FOR FORMING A STENT OF A DESIRED LENGTH AT AN ENDOLUMINAL SITE

(75) Inventor: Richard W. Ducharme, Winston-Salem, NC (US)

(73) Assignee: Wilson-Cook Medical Inc., Winston-Salem, NC (US)

(*) Notice: Subject to any disclaimer, the term of this patent is extended or adjusted under 35 U.S.C. 154(b) by 98 days.

(21) Appl. No.: 11/867,515

(22) Filed: Oct. 4, 2007

(65) Prior Publication Data

US 2009/0093889 A1    Apr. 9, 2009

(51) Int. Cl.
*A61M 29/00* (2006.01)
*A61F 2/06* (2006.01)
*A61F 2/04* (2006.01)
*A61F 2/84* (2006.01)

(52) U.S. Cl. .............. 606/200; 623/1.11; 623/23.7

(58) Field of Classification Search .......... 623/1.11, 623/1.12, 1.18, 1.22, 1.2, 23.64, 23.69, 23.7; 604/8; 606/159, 200

See application file for complete search history.

(56) References Cited

U.S. PATENT DOCUMENTS

| | | |
|---|---|---|
| 4,643,716 A | 2/1987 | Drach |
| 4,895,560 A | 1/1990 | Papantonakos |
| 4,926,858 A | 5/1990 | Gifford, III et al. |
| 4,950,277 A | 8/1990 | Farr |
| 4,966,604 A | 10/1990 | Reiss |
| 5,098,776 A | 3/1992 | Kobayashi et al. |
| 5,217,474 A | 6/1993 | Zacca et al. |
| 5,314,438 A | 5/1994 | Shturman |
| 5,395,311 A | 3/1995 | Andrews |

(Continued)

FOREIGN PATENT DOCUMENTS

DE    9409161 U1    8/1995

(Continued)

OTHER PUBLICATIONS

The International Search Report and the Written Opinion of the International Searching Authority dated Aug. 8, 2008 for International Patent Application No. PCT/US2008/078360.

(Continued)

*Primary Examiner*—Thomas J Sweet
*Assistant Examiner*—Yashita Sharma
(74) *Attorney, Agent, or Firm*—Brinks Hofer Gilson & Lione

(57) ABSTRACT

Described herein are a system and a method for forming a stent of a desired length endoluminally. The system includes an elongate stent body and an outer sheath overlying the stent body. An endoluminal cutting mechanism is operatively connected to a drive cable in communication with the outer sheath. The cutting mechanism is configured to cut the stent body in response to motion of the drive cable. The method of forming the stent of a desired length endoluminally includes directing a system including an elongate stent body and an outer sheath overlying the stent body into a body lumen, positioning the stent body at an endoluminal site, and severing the stent body to form a stent of a desired length at the endoluminal site. An undeployed portion of the stent body remains in the outer sheath for optional deployment in a subsequent severing operation.

13 Claims, 9 Drawing Sheets

U.S. PATENT DOCUMENTS

| | | | |
|---|---|---|---|
| 5,628,746 A | 5/1997 | Clayman | |
| 5,716,410 A | 2/1998 | Wang et al. | |
| 5,810,806 A * | 9/1998 | Ritchart et al. | 606/45 |
| 5,827,310 A | 10/1998 | Marin et al. | |
| 5,876,450 A | 3/1999 | Johlin, Jr. | |
| 5,893,859 A | 4/1999 | Marin et al. | |
| 5,964,744 A | 10/1999 | Balbierz et al. | |
| 6,050,995 A | 4/2000 | Durgin | |
| 6,168,605 B1 | 1/2001 | Measamer et al. | |
| 6,306,151 B1 | 10/2001 | Lary | |
| 6,500,186 B2 | 12/2002 | Lafontaine et al. | |
| 6,533,801 B2 * | 3/2003 | Wallace et al. | 606/200 |
| 6,602,250 B2 | 8/2003 | Karpiel et al. | |
| 6,711,444 B2 | 3/2004 | Koblish | |
| 6,720,402 B2 | 4/2004 | Langer et al. | |
| 6,796,989 B2 | 9/2004 | Uflacker | |
| 6,858,680 B2 | 2/2005 | Gunatillake et al. | |
| 7,083,641 B2 * | 8/2006 | Stinson et al. | 623/1.34 |
| 7,087,078 B2 | 8/2006 | Hildebrand et al. | |
| 2003/0130683 A1 * | 7/2003 | Andreas et al. | 606/200 |
| 2003/0135222 A1 | 7/2003 | Baska | |
| 2003/0216804 A1 | 11/2003 | DeBeer et al. | |
| 2004/0015187 A1 | 1/2004 | Lendlein et al. | |
| 2004/0172121 A1 * | 9/2004 | Eidenschink et al. | 623/1.11 |
| 2004/0249441 A1 * | 12/2004 | Miller et al. | 623/1.15 |
| 2004/0260384 A1 * | 12/2004 | Allen | 623/1.12 |
| 2005/0075723 A1 * | 4/2005 | Schroeder et al. | 623/2.1 |
| 2005/0240277 A1 | 10/2005 | Aliski et al. | |
| 2005/0267570 A1 | 12/2005 | Shadduck | |
| 2006/0167538 A1 | 7/2006 | Rucker | |
| 2006/0178699 A1 | 8/2006 | Surti | |

FOREIGN PATENT DOCUMENTS

| | | |
|---|---|---|
| WO | WO 98/30156 A1 | 7/1998 |

OTHER PUBLICATIONS

Cha, D. I.; Kim, H. Y.; Lee, K. H.; Jung, Y. C.; Cho, J. W.; Chun, B. C. "Electrospun Nonwovens of Shape-Memory Polyurethane Block Copolymers," *Journal of Applied Polymer Science*, 2005, 96, 460-465.

Yakacki, C. M.; Shandas, R.; Lanning, C.; Gall, K. "Free Recovery Effects of Shape-Memory Polymers for Cardiovascular Stents," *Mater. Res. Soc. Proc.*, 2006, 898E, 1-8.

"AcuSnare® One Piece Disposable Snares," *Cook Medical Endoscopy*, http://www.cookmedical.com/esc/dataSheet.do?id=721, Apr. 2, 2007, p. 1 of 2.

"Biliary and Pancreatic Stents," *Gastrointestinal Endoscopy*, www.giejournal.org, 2006, 63:7, 910-919.

"CaloMER™ Shape-Memory Thermoplastic," http://www.polymertech.com/materials/calomer.html, Oct. 10, 2006, 4 pages.

"Cook Flexible Myocardial Biopsy Forceps," *Cook Diagnostic and Interventional Products Brochure*, 2000, 1 page.

"Sonnet™ Polypectomy Snare," *Cook Endoscopy Brochure*, 6 pages.

\* cited by examiner

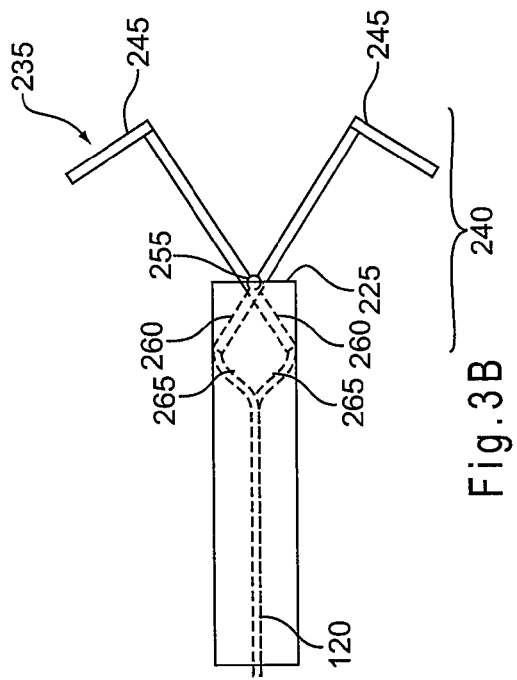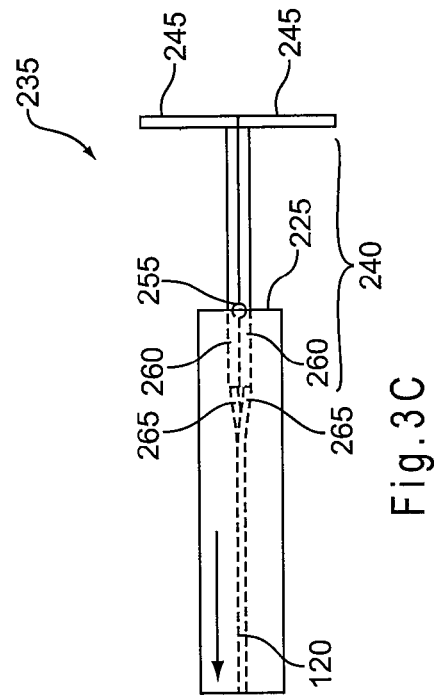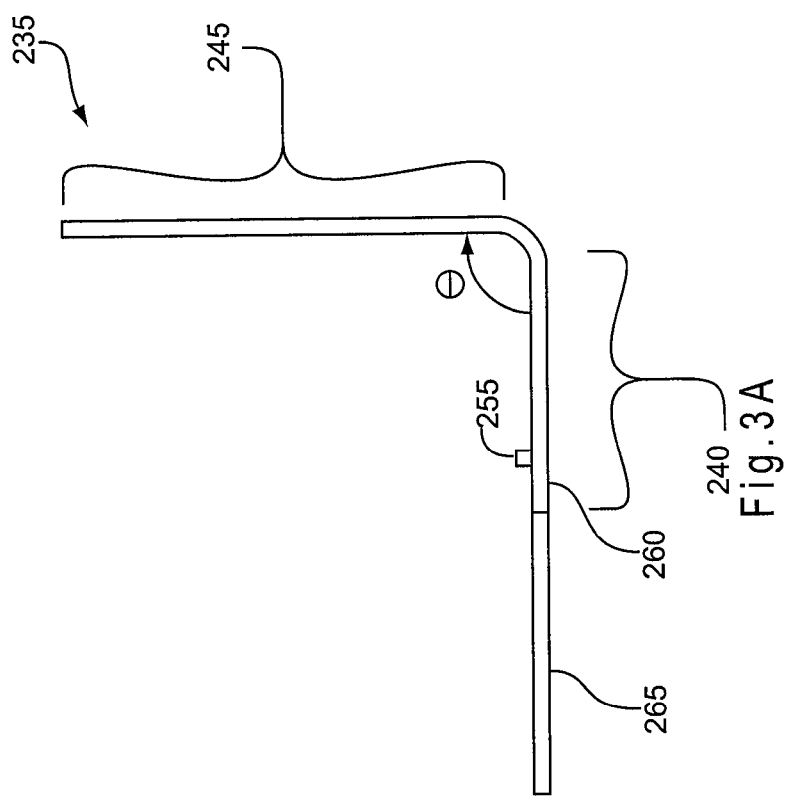

SYSTEM AND METHOD FOR FORMING A STENT OF A DESIRED LENGTH AT AN ENDOLUMINAL SITE

TECHNICAL FIELD

The present disclosure is related generally to medical devices and more particularly to deployment systems for stents.

BACKGROUND

Biliary and pancreatic cancers often are diagnosed when the patient presents specific symptoms characteristic of a blockage of either the patient's bile and/or pancreatic duct, such as jaundice. Typically, by the time symptoms appear in the patient, a tumor in the bile or pancreatic duct is at an advanced stage and is therefore inoperable. As a result, management of the cancer usually focuses on palliation of the symptoms. As an alternative to surgical bypass procedures for palliation, a stent or endoprosthesis may be positioned through the obstructed area (stricture) so as to maintain a pathway for fluid flow.

Typically, stents used for drainage in the biliary tract are nonexpandable tubular structures formed from biocompatible polymers. Before endoscopic placement of a biliary or pancreatic stent, endoscopic retrograde cholangiopancreatography (ERCP) may be performed to evaluate the biliary tree and the pancreatic duct. Preferably, the location, length, and proximal extent of the stricture are determined, and a stent of an appropriate length is selected for deployment into the duct. Because a fluoroscopic projection of the duct shows detail in only two dimensions, however, and the duct extends along three dimensions, it may be difficult for the clinician to accurately assess the stent length needed for placement into the duct.

To deploy the stent, a wire guide may be passed into the duct and across the stricture, and the stent may be advanced over the wire guide and into the duct of interest. A distal end of the stent may be directed across the ductal obstruction, while a proximal end of the stent remains proximal of the stricture, preferably protruding into the duodenum.

In some cases, it may be desirable or necessary to place more than one stent at the obstructed site to expand the stricture commensurate with the diameter of the duct. Accordingly, once the first stent is placed, a second stent may be introduced into the patient and delivered using the same procedure. After placement of the second stent, additional stents may be separately introduced into the patient and delivered to the treatment site in order to open the obstructed region to the desired diameter. Depending on the size of the duct and the diameter of the stents, it may be necessary to place two to six stents across the obstructed region.

The process of delivering and deploying multiple stents into the pancreatic or bile duct can be tedious and slow. It would be desirable to have a system and method that allowed for more efficient placement of multiple stents. It would also be beneficial if fewer stents were needed to open larger diameter ducts. In addition, it would be advantageous if a clinician could more accurately assess the stent length needed for placement into the duct.

BRIEF SUMMARY

Described herein are a system and a method for forming at least one stent of a desired length at an endoluminal site. The system and method may advantageously allow a clinician to place one or more stents of customized lengths at a stricture in a body vessel or duct, such as the pancreatic or bile duct. The system and method may be particularly advantageous for the placement of multiple stents in the duct of interest. In addition, the system and method may allow larger diameter ducts to be opened with fewer stents.

The system includes, according to one embodiment, an elongate stent body and an outer sheath overlying the stent body. An endoluminal cutting mechanism is operatively connected to a drive cable in communication with the outer sheath. The endoluminal cutting mechanism is configured to sever the stent body in response to motion of the drive cable.

The system includes, according to another embodiment, an elongate stent body severable into a deployed portion and an undeployed portion thereof. The deployed portion is a stent of a desired length. The system also includes an outer sheath overlying the stent body, and an endoluminal cutting mechanism disposed adjacent to the stent body. Upon severing of the stent body by the endoluminal cutting mechanism, the stent is deployed at an endoluminal site and the undeployed portion of the stent body remains in the outer sheath. The undeployed portion is configured to be deployed in a subsequent severing operation.

The method includes directing a deployment system including a stent body and an outer sheath overlying the stent body into a body lumen. The stent body is positioned at an endoluminal site within the body lumen and is severed to form a stent of a desired length at the endoluminal site. An undeployed portion of the stent body remains in the outer sheath. Preferably, the positioning of the stent body at an endoluminal site and the severing of the stent body are carried out more than one time to form more than one stent of a desired length from the stent body.

BRIEF DESCRIPTION OF THE DRAWINGS

FIG. 3A is a side view of the cutting mechanism of FIG. 2; FIGS. 3B and 3C are top views of the cutting mechanism of FIG. 2;

DETAILED DESCRIPTION

Figure 1:
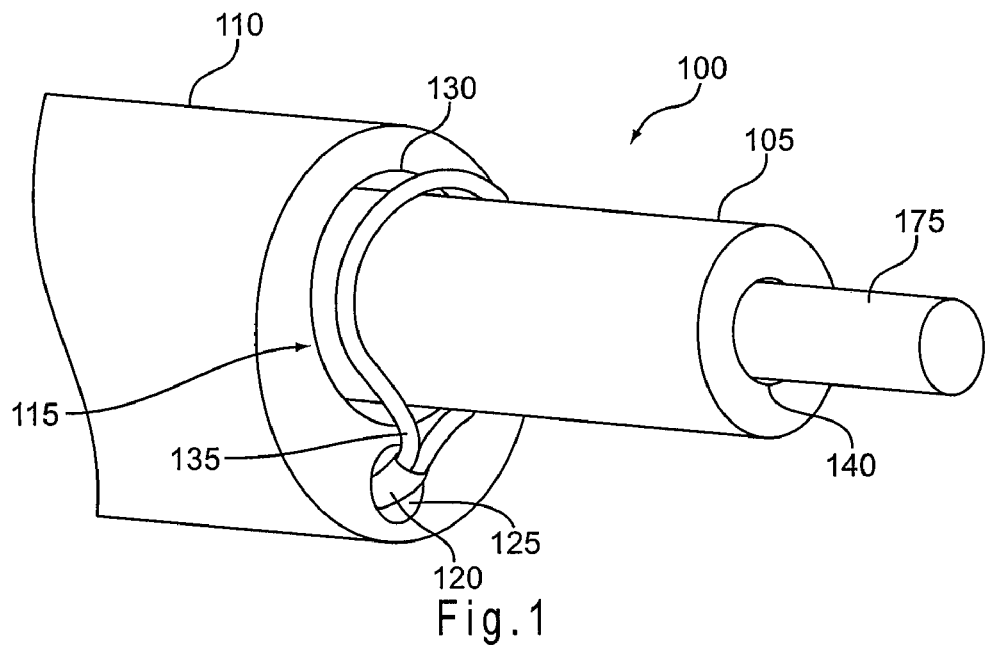
FIG. 1 is a perspective view of a portion of a deployment system including a cutting mechanism according to one embodiment.

FIG. 1 shows a perspective view of one embodiment of a system for forming a stent of a desired or customized length at an endoluminal site ("endoluminally"). The system may be particularly useful for stents placed in the biliary or pancreatic duct. However, the system may also be useful for stents placed in other locations within the body. In the description below, the term "stent body" will be used in reference to the body of material from which a stent of a desired length is cut.

Referring to FIG. 1, the system 100 includes a stent body 105 and an outer sheath 110 overlying the stent body 105. Preferably, the stent body 105 has a tubular or rod-like shape and is formed of a biocompatible polymer, as will be discussed further below. A cutting mechanism 115 extends from a distal end of a drive cable 120 that is preferably slideably disposed within a secondary lumen 125 of the outer sheath 110. The secondary lumen 125 containing the drive cable 120 is preferably separate from a primary lumen 130 of the outer sheath 110 that contains the stent body 105. The secondary lumen 125 may be smaller in diameter than the primary lumen 130.

The outer sheath may alternatively include a first tubular body and a second tubular body adjoined thereto, where the first tubular body contains the primary lumen and the second tubular body contains the secondary lumen. The second tubular body may be bonded, affixed, or otherwise attached to the first tubular body. One or both of the first tubular body and the second tubular body may be discontinuous along a length of the stent body.

The cutting mechanism 115 is configured to cut the stent body 105 endoluminally in response to motion of the drive cable 120. Preferably, the cutting mechanism 115 is disposed outside a lumen 140 of the stent body 105. Accordingly, the cutting mechanism 115 preferably cuts the stent body 105 to length by first penetrating an outer surface thereof. It is also preferred that the cutting mechanism 115 is configured to cut the stent body in response to a proximally-directed motion of the drive cable 120. In alternative embodiments, however, a distally-directed motion of the drive cable 120 may be employed to actuate the cutting mechanism 115.

According to the embodiment of FIG. 1, the cutting mechanism may be a wire 135 in a snare or noose configuration. The wire 135 is attached to the drive cable 120 and includes a bend so that the wire 135 can be looped about the stent body 105. Snare geometries known in the art, such as circular, oval, and hexagonal configurations, may be suitable for the loop of the wire 135. Preferably, the wire 135 forms a continuous loop about the stent body 105, although non-continuous wire configurations (e.g., hook-like configurations) are also possible. When the drive cable 120 is moved in a proximal direction (retracted), the wire 135 forcibly contacts an external surface of the stent body 105. With continued retraction of the drive cable 120, the wire 135 can penetrate and pass through an external surface of the stent body 105 and ultimately cut entirely through the thickness thereof. The location of the cut on the stent body 105 is selected to form a stent of an appropriate length for placement across a stricture in the pancreatic or bile duct.

It may be advantageous for the wire 135 to have a sufficient stiffness and resilience to maintain and/or readily return to the snare, noose, or hook-like configuration after cutting. For example, after the stent body is placed at a treatment site and cut to form the stent of a given length, a resilient wire snare that recovers its shape may be readily repositioned over the stent body disposed proximal to the cut stent. The stent body may then be advanced to the treatment site through the wire noose and cut to form another stent of a given length. In this fashion, multiple stents may be delivered to the treatment site and cut to length endoluminally. A stiff wire may also be more effective at penetrating the external surface of the stent body. Accordingly, the wire 135 may be made of a metal or metal alloy, such as stainless steel or nickel-titanium (e.g., superelastic or linear elastic Nitinol). Preferably, the metal or alloy is biocompatible. Techniques known in the art for making endoscopic snares may be adapted to form the wire cutting mechanism of the present disclosure.

Figure 2:
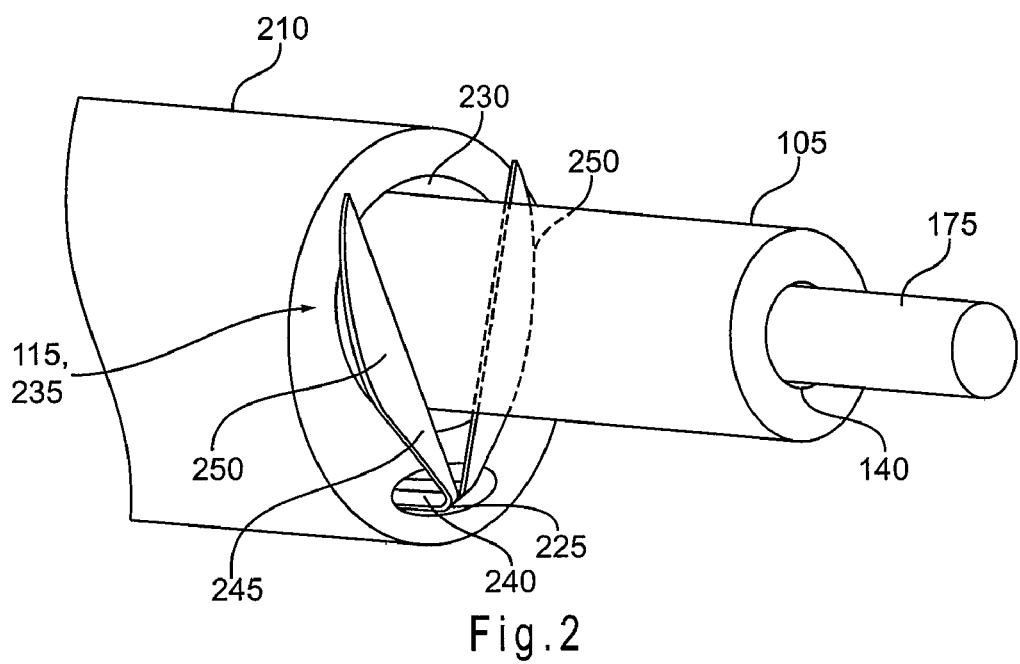
FIG. 2 is a perspective view of a portion of a deployment system including a cutting mechanism according to another embodiment.

According to an alternative embodiment shown in FIG. 2, the cutting mechanism 115 is a scissor mechanism 235 disposed adjacent to the stent body 105. The scissor mechanism 235 includes a hinged portion 240 and a cutting portion 245 disposed at an angle $\theta$ with respect to the hinged portion 240, as shown in FIGS. 2 and 3A. Two oppositely disposed blades 250 are crossed and connected to form the hinged portion 240, and distal ends of the blades 250 are bent at an angle $\theta$ to form the cutting portion 245. The cutting portion 245 of the blades 250 may be straight, as shown in FIG. 3A, or curved. Proximal ends 260 of the blades 250 are attached to the drive cable 120 via a wire or other connector 265 extending from each proximal end 260, as shown in FIGS. 3B and 3C. The scissor mechanism 235 may be formed of stainless steel, superelastic nickel-titanium, or another biocompatible material. Techniques known in the art for making forceps and laparoscopic scissors may be adapted to make the scissor mechanism of the present disclosure.

Preferably, the cutting portion 245 of the scissor mechanism 235 has a length that is equal to or larger than the outer diameter of the stent body 105. For example, the length of the cutting portion 245 may range from about 0.5 mm to about 3.5 mm. Referring to the embodiment shown in FIG. 3A, the distal ends of the blades 250 may be bent at a right angle ($\theta=90°$) such that the cutting portion 245 of the blades 250 is in a vertical position when the hinged portion 240 of the blades is in a horizontal position. Other angles $\theta$ between the hinged portion 240 and the cutting portion 245 may also be used. Preferably, the angle $\theta$ between the hinged portion 240 and the cutting portion 245 is a right angle or an obtuse angle (i.e., $\geq 90°$). The scissor mechanism 235 may alternatively be configured such that the cutting portion 245 includes the connection point (hinge) 255 of the two blades 250, and the hinged portion 240 includes only proximal ends or handles 260 of the blades 250.

As in the previous embodiment, the scissor mechanism 235 may be configured to cut the stent body 105 endoluminally in response to motion of the drive cable 120. When the drive cable 120 is moved in a proximal direction (retracted), the proximal ends and distal ends of the blades 250 are respectively pulled together from an open position and the cutting portion 245 of the scissor mechanism 235 forcibly contacts an external surface of the stent body 105. With continued retraction of the drive cable 120, the blades 250 can penetrate and pass through an external surface of the stent body 105 and cut entirely through the thickness thereof. The location of the cut on the stent body 105 may be selected such that a stent of a desired length is formed within a body lumen. Once the stent has been cut to length, the drive cable 120 can be moved in a distal direction to cause the blades 250 to return to the open position. If desired, the stent body 105 may again be passed through the deployment system and placed at the treatment site, and then the drive cable 120 may be retracted a second time to cut the stent body 105 and form a second stent of an appropriate length. The procedure may be repeated multiple times to deploy multiple stents.

Preferably, the cutting mechanism 115 is configured for cleanly severing the stent body 105. In the case of the wire 135 of the first embodiment, a fine-gauge round wire 135 may be suitable as a cutting mechanism. Alternatively, the wire 135 may include a sharp edge along at least a portion of a length thereof to facilitate engaging and penetrating the external surface of the stent body 105 when the wire 135 is forced into contact with the surface. For example, the wire 135 may be a flat wire including four abrupt edges. It is also contemplated that a blade may be attached to the wire 135 to provide a sharp edge. In the case of the scissor mechanism of the second embodiment, the blades 250 may include sharpened, serrated or overlapping inner edges for easier penetration of the stent body 105.

To further improve the ease with which the cutting mechanism 115 may sever the stent body 105, the cutting mechanism 115 may be configured to generate heat during the cutting process, thereby softening, melting or vaporizing the material of the stent body 105 as the cutting mechanism passes therethrough. An electrical power source located outside the body lumen may be electrically connected with a proximal end of the drive cable, and a radiofrequency (RF) current may be passed through the drive cable and cutting mechanism. RF energy applied between the cutting mechanism, stent body, and a grounding pad can provide a cutting arc. The cutting arc passes through the stent material as the cutting mechanism severs the stent body. The current flows into the patient's body to a grounding pad and completes a monopolar circuit. The stent acts as a resistor in the monopolar circuit and provides the greatest resistance at the contact point between the cutting mechanism and the stent, where the current density is the greatest. Monopolar and bipolar cutting devices (e.g., electrosurgical snares) are known in the art for excising tissue. Both monopolar and bipolar approaches are applicable to the present cutting mechanism. In the bipolar approach, two electrically insulated drive cables may be employed in lieu of a single drive cable (monopolar approach), and RF energy may be applied across the two cables, which serve as electrodes. The electrically insulated drive cables, which may include a Teflon or parylene coating, for example, may be disposed in parallel to each other or twisted together to form a cohesive unit. The cutting process may be further improved by forming the stent body 105 from a polymer with a low electrical resistivity and/or a low melting temperature. It also may be advantageous to incorporate biocompatible conductive particles (e.g., silver particles) within the stent material during fabrication of the stent body to reduce the electrical resistivity of the polymer.

The diameter of the drive cable 120 is preferably large enough to provide sufficient stiffness during endoluminal use but small enough so as to not detrimentally increase the profile of the deployment system 100. To accommodate a larger diameter cable, a larger secondary lumen 125 of the outer sheath 110 may be needed, and the larger secondary lumen 125 may in turn increase the requisite diameter of the outer sheath 110. A high stiffness of the drive cable 120 may be advantageous to facilitate distal motion of the cable 120 for repositioning the cutting mechanism 115 after a first stent body 105 is placed at the treatment site and cut endoluminally. Preferably, the drive cable 120 may have a diameter of from about 0.3 mm to about 0.5 mm. For example, the diameter may be about 0.4 mm. The drive cable 120 may be fabricated from stainless steel or another biocompatible metal or alloy.

Preferably, the drive cable 120 has a length sufficient for the motion thereof to be actuated from outside a body lumen. Preferably, a proximal end of the drive cable 120 is disposed outside a patient's body and a distal end of the drive cable 120 extends to an endoluminal position adjacent to a treatment site. Accordingly, the drive cable 120 may range from about 150 cm to about 300 cm in length. Preferably, the length of the drive cable 120 is from about 200 cm to about 250 cm.

Figure 4A:
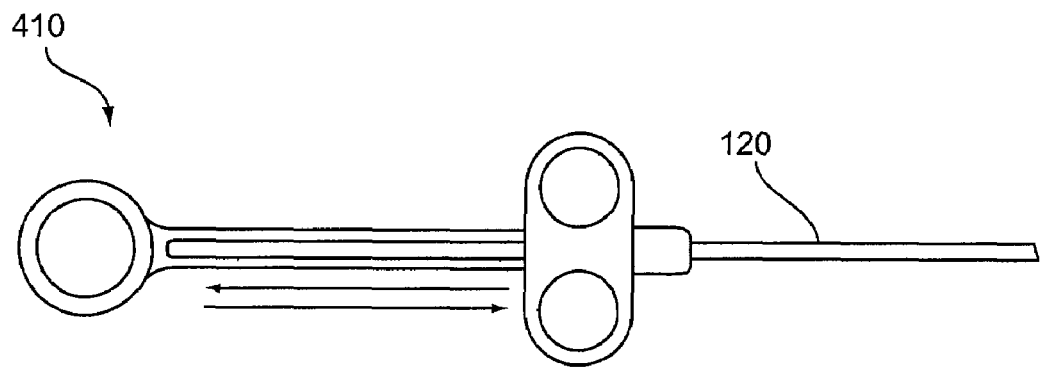
FIG. 4A shows a proximal actuator according to a first embodiment.
Figure 4B:
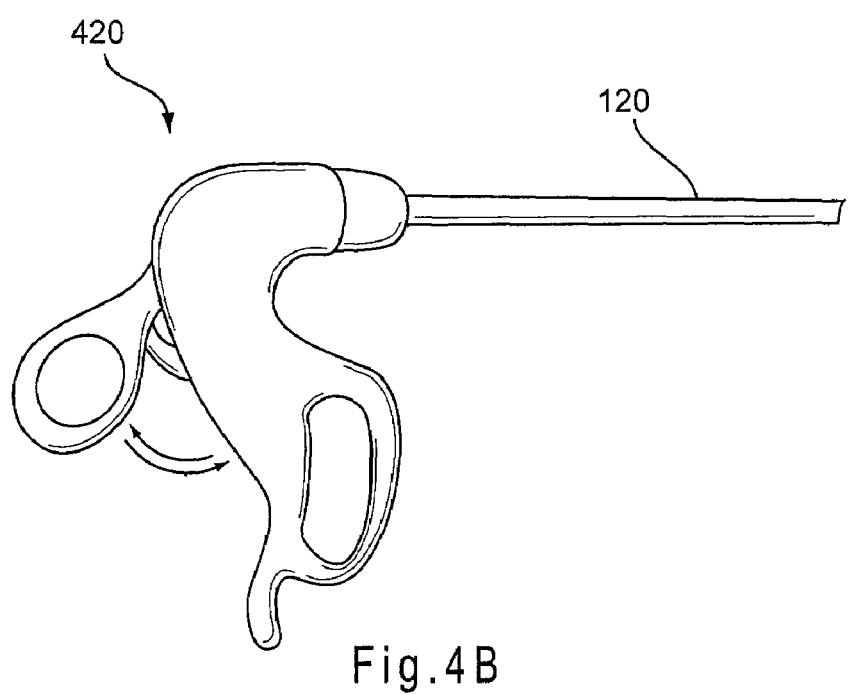
FIG. 4B shows a proximal actuator according to a second embodiment.

According to one embodiment, a proximal actuator may be disposed outside the body lumen and in communication with the proximal end of the drive cable 120. The proximal actuator may improve the ease and control with which the proximal end of the drive cable 120 may be manually manipulated by the clinician. The proximal actuator may be a handle that allows the proximal end of the drive cable to be translated proximally and distally. Referring to FIG. 4A, the handle 410 itself may move proximally and distally to actuate the drive cable translation. Alternatively, as shown in FIG. 4B, the handle 420 may have a scissor-like actuation mechanism. In another example, the handle may rotate or turn in a crank-like fashion to actuate the motion of the drive cable 120. It is also envisioned that the proximal actuator may allow the drive cable 120 to be translated semi-automatically (e.g., by the push of a button). Proximal actuators (i.e., handles) known in the art for snares, forceps and laparoscopic scissors used to hold and cut tissue may be adapted for use with the cutting mechanism of the present disclosure.

It is preferred that the system 100 includes one or more radiopaque markers that facilitate monitoring of the procedure from outside the patient's body. The radiopaque markers may be attached to or integrated with the stent body 105, the cutting mechanism 115, and/or the distal end of the drive cable 120, for example. The radiopaque markers may include one or more elements selected from the group consisting of Pt, Pd, W, Ta, Au, Ag, Bi, Hf, Re, Os, Ir, Ru, and Rh, for example. One or both of the stent body 105 and the cutting mechanism 115 may also or alternatively be formed of or include a radiopaque material, such as a radiopaque metal or alloy. The distal end of the drive cable 120 may also be formed of a radiopaque material. Accordingly, a clinician may manipulate a proximal end of the drive cable 120 while viewing the internal positioning of the cutting mechanism 115, the distal end of the drive cable 120, and/or the stent body 105 with x-ray fluoroscopy or a similar imaging technique. Exemplary radiopaque materials may include one or more elements selected from the group consisting of Pt, Pd, W, Ta, Au, Ag, Bi, Hf, Re, Os, Ir, Ru, and Rh.

It may be advantageous for the stent body 105 to include a discrete or continuous marking pattern along its length. The pattern may be formed, for example, by biocompatible inks applied to the stent body 105 that are visually observable by the clinician as the stent body is directed through the endoscope. In another example, the pattern may be formed by radiopaque markers that are attached to or integrated with the stent body 105 and visible from within a body duct using fluoroscopy. The stent body may include, for example, a spiral marking pattern, a ruler-like numbering system, visible or radiopaque bands, or another regular arrangement of markers useful for estimating length along the stent body 105. Such a marking pattern may enable the clinician to monitor the length of the stent body 105 passed through the endoscope and into the duct of interest. The clinician may also be able to gauge the length of the stent 105*a* deployed at the treatment site and the length of the stent body 105 remaining in the outer sheath 110 after actuation of the cutting mechanism 115.

As mentioned above, the stent body 105 may be formed of a biocompatible polymer. The stent body 105 may be fabricated from the polymer by extrusion and/or molding techniques known in the art. Preferably, the stent body is formed of a shape memory polymer, such as a shape memory polyurethane. A shape memory polymer can recover a previous configuration upon heating above a first transition temperature. Accordingly, with appropriate selection of the first transition temperature, the stent body may have a first configuration during delivery and a second configuration once deployed at the treatment site. Preferably, the first transition temperature is at or below body temperature (37° C.).

According to one embodiment, the shape memory polymer may be formed of a segregated linear block co-polymer that includes hard segments and soft (or switching) segments. Examples of suitable polymer segments are provided in U.S. Pat. No. 6,720,402, filed on May 8, 2002, which is hereby incorporated by reference in its entirety. The hard segments may be crystalline or amorphous and have the first transition temperature (e.g., melting point or glass transition temperature), and the switching segments may be crystalline or amorphous and have a second transition temperature (e.g., melting point or glass transition temperature). Preferably, the second transition temperature is lower than the first transition temperature. Stents or stent bodies formed of a shape memory polymer may be shaped or molded to the first configuration at a temperature above the first transition temperature, cooled to a temperature below the second temperature, deformed (strained) into the second configuration for delivery into a body vessel, and then, at the treatment site, warmed to a temperature above the first transition temperature to recover the first configuration. It is contemplated that application of a stimulus other than heat (e.g., ionic change, pH, light, electric field, magnetic field, ultrasound) may be alternatively employed to cause the shape memory polymer of the stent to return to the first configuration.

Figure 5:
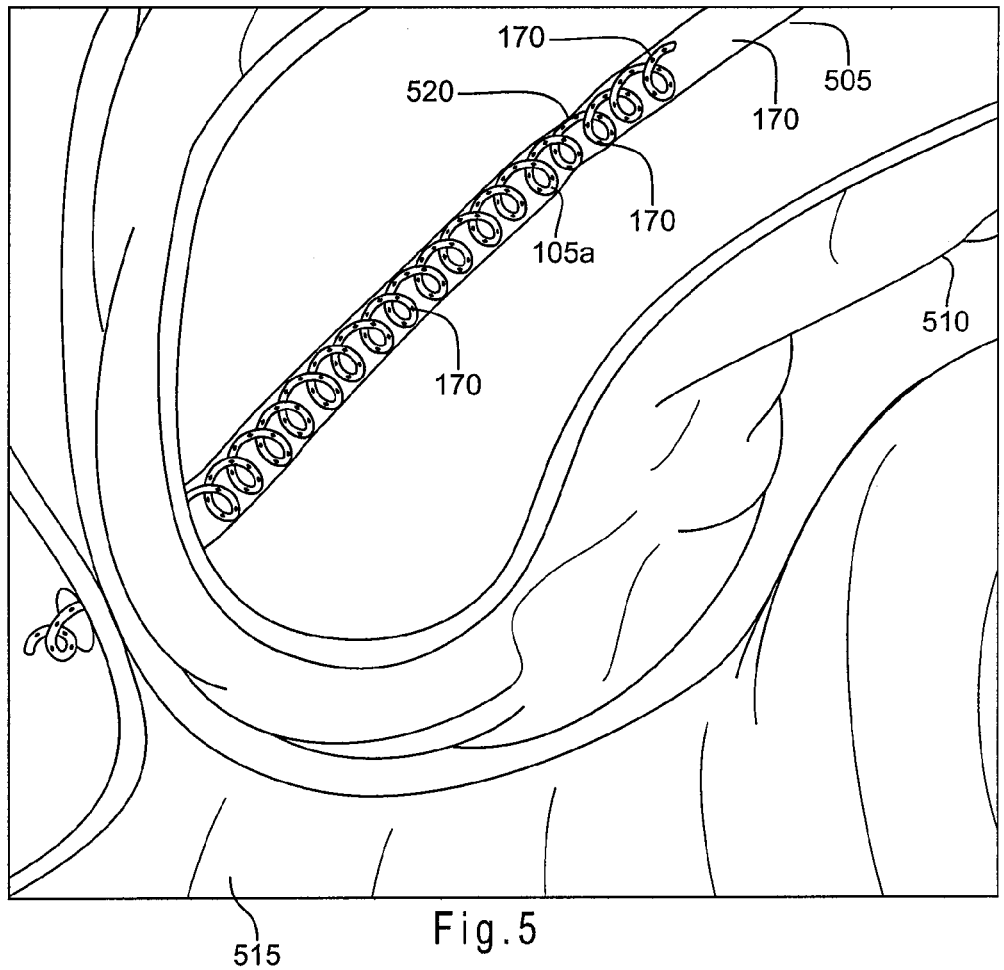
FIG. 5 is a schematic showing a stent according to one embodiment deployed in the pancreatic duct.
Figure 6:
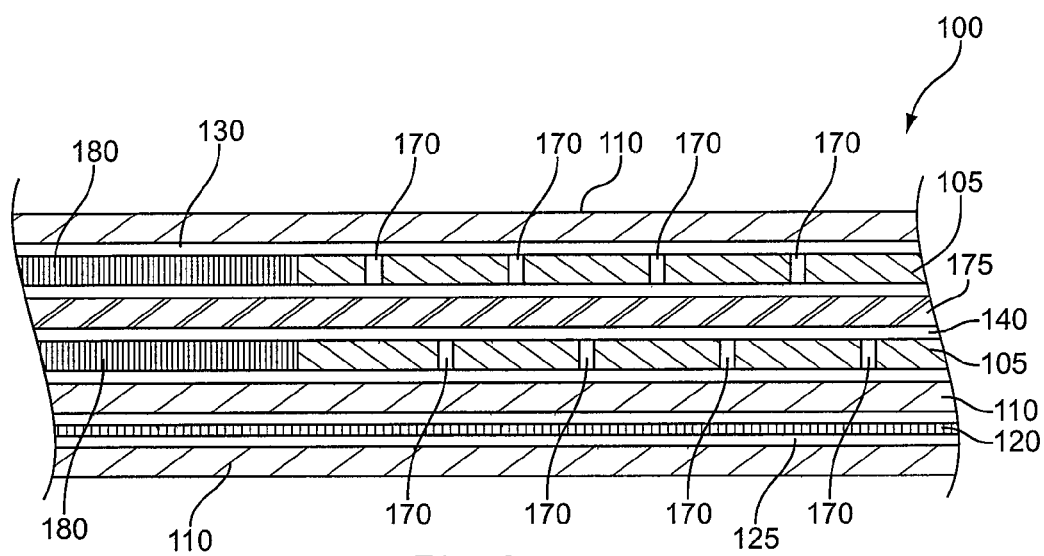
FIG. 6 is a longitudinal cross-sectional view of a portion of the deployment system.

Preferably, the first configuration (deployment configuration) of the stent body 105 and stent 105a described herein is a coiled or corkscrew geometry, and the second configuration (delivery configuration) is a substantially straight but pliable configuration, as indicated for example in FIGS. 5 and 6. A stent formed of a shape memory polymer having a transition temperature equal to body temperature or slightly below may begin to recover the coiled geometry as it warms up to body temperature (37° C.) during or following deployment at the treatment site (stricture), as will be discussed further below. Such a coiled configuration may be advantageous for facilitating fluid flow through the duct. The coiled geometry also may be advantageous for anchoring the stent in place in the duct. Typically, presently available stents are substantially straight or bent at an angle with flaps or pigtails near one or both ends to minimize migration of the stent within the duct. The coiled geometry of the stent 105a described herein is effectively a series of pigtails, and thus the deployed stent 105a advantageously includes one or more retention members regardless of the length to which it is cut endoluminally.

According to alternative embodiments, the second configuration may be a compressed coiled geometry for delivery, and the first configuration may be a larger-diameter coiled geometry for deployment at the treatment site. Alternatively, the second configuration may be another compressed shape and the first configuration may be a radially-expanded version of the second configuration. It is also envisioned that, in the first configuration, the stent may be substantially straight or bent at an angle and include flaps or pigtails at one or more locations along the length for securing the stent in place in the duct.

Once situated in the duct of interest, the stent body may be cut to form a stent of a suitable length. FIG. 5 shows an exemplary stent 105a in a deployed configuration (e.g., coiled configuration) within the pancreatic duct 505 of the pancreas 510. The length of the stent 105a in the deployed configuration (e.g., coiled configuration) is preferably longer than the distance from the duodenum 515 to the treatment site or stricture 520 within the duct 505. Typically, the length of the stent 105a is about 1 cm longer than the distance from the duodenum 515 to the proximal margin of the stricture 520. For example, if the stricture 520 lies within the pancreatic duct 505 about 6.0 cm away from the duodenum 515, a stent 105a of about 6.5 cm or 7.0 cm in length may be appropriate. According to another embodiment, the length may be longer than the distance from the duodenum 515 to the terminus or tail of the duct 505. For example, in the case of a pancreatic duct 505 measuring about 16.0 cm in length, a stent 105a of about 16.5 cm or 17.0 cm in length may be appropriate.

According to one embodiment, the stent body 105 may include a lumen 140 sized to receive a wire guide, as described further below. The stent body 105 may also include a plurality of drainage holes 170 along its length, as shown in FIGS. 5 and 6, to enhance drainage through the lumen of the deployed stent 105a. Regularly spaced drainage holes may also function as a marking pattern, as described further above. According to an alternative embodiment, the stent body may take the form of a solid rod that does not include a wire guide lumen. Drainage through the duct may be achieved by virtue of the coiled geometry of the stent 105a when in position in the duct.

The diameter of the stent 105a in the coiled configuration (i.e., coil diameter) may be substantially greater than the diameter of the stent body 105 when disposed within the outer sheath. For example, an uncoiled stent body of 3 F in diameter may attain a coil diameter of 9 F when deployed in the duct. The difference between the diameter of the undeployed stent body and the coil diameter may be even greater when solid rod stents are used. Since such stents do include a wire guide lumen, they may have a smaller profile within the outer sheath. The undeployed diameter of such stent bodies may be less than 3 French, or less than 1 French. By employing straight stents that attain a coiled geometry in the duct, it may be possible to open larger diameter ducts with fewer stents.

As described above, the outer sheath 110, 210 preferably includes a primary lumen 130, 230 that overlies the stent body 105 and a secondary lumen 125, 225 that overlies the drive cable 120, 220. The primary lumen 130, 230 may have a size sufficient to accommodate a stent body 105 of from 1 French or less in diameter to 10 French in diameter, according to one embodiment. The secondary lumen 125, 225 may range in diameter from about 0.5 mm to about 1.0 mm to accommodate the drive cable 120. At a distal end of the outer sheath 210, the secondary lumen 225 may have an expanded size and a non-circular transverse cross-section to accommodate, for example, the hinged portion 240 of the scissor mechanism 235, as shown for example in FIG. 2. According to an alternative embodiment, the outer sheath may include a single lumen that houses both the stent body and the drive cable of the cutting mechanism.

The outer sheath 110, 210 is preferably formed of a biocompatible polymer, such as, for example, nylon, polyethylene, or polytetrafluoroethylene (PTFE). The outer sheath may include a reinforcement structure over all or a portion of the length thereof for kink resistance and column strength. It may be particularly advantageous to include the reinforcement structure at the distal end of the sheath. The reinforcement structure may be, for example, a coil embedded within a wall of the sheath and disposed in a helical or other suitable configuration, or a metal cap overlying the distal end of the sheath and including one or more lumens for passage of the stent body and the drive cable. It is also possible that the outer sheath may have the form of a coil or a Teflon-coated coil.

According to one embodiment, the system 100 for deploying the stent 105 within a body vessel or duct may include one or both of a wire guide 175 and pushing catheter 180, as shown in FIG. 6. A guiding catheter may also be used. The stent body 105 may have an outer diameter in the range of from about 1 French to about 12 French. The stent body 105 may also have a lumen 140 sized to receive the wire guide 175 and, in some embodiments, the guiding catheter. The wire guide may be about 0.035 inch in diameter, or another suitable size. Generally, guiding catheters are used with larger diameter stents. The guiding catheter may have an outer diameter or French size that can be accommodated within the lumen 140 of the stent body. The stent body 105 may include a distal region having a reduced inner diameter that serves as a distal stop when the guiding catheter is inserted into the stent body 105. The guiding catheter may have an outer diameter that is similar to the outer diameter of the pushing catheter. If a guiding catheter is not used, the outer diameter of the stent body 105 may be similar to the outer diameter of the pushing catheter 180.

A method of forming and deploying at least one stent of a desired length endoluminally is described herein. The method includes directing a deployment system into a body lumen. The deployment system preferably includes a stent body and an outer sheath overlying the stent body. The stent body is positioned at a treatment site within the body lumen, and the stent body is severed to form a stent of a desired length. Preferably, the deployment system includes a cutting mechanism operatively connected to a drive cable. The drive cable may be moved (e.g., retracted) to actuate the cutting mechanism to sever the stent.

Figure 7A:
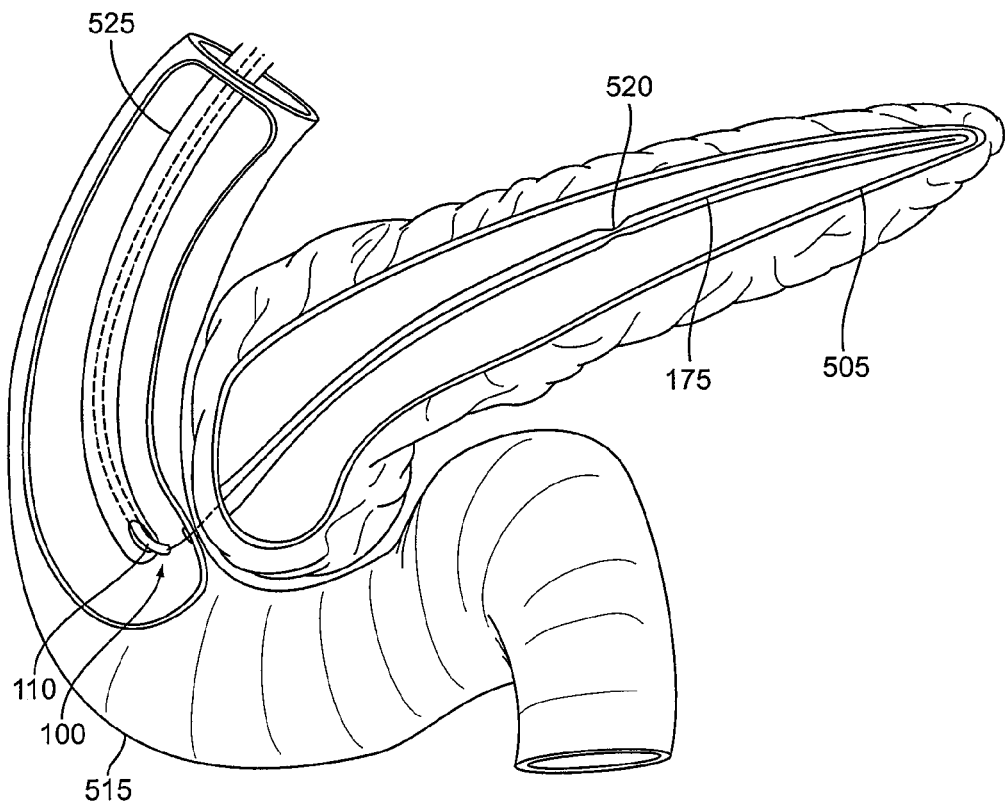
FIG. 7A is a schematic showing placement of a wire guide into the pancreatic duct according to one aspect of the method.
Figure 7B:
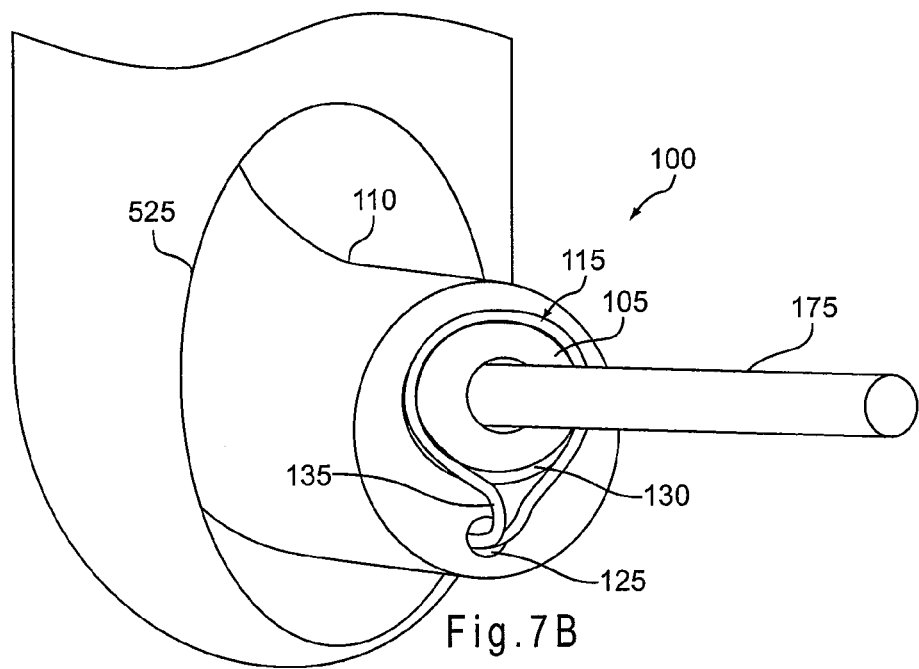
FIG. 7B is a close-up view of a portion of the deployment system used in FIG. 7A.

According to one aspect of the method, the stent body may be positioned in the pancreatic or biliary duct. Referring to FIG. 7A, a wire guide 175 may be advanced through an endoscope 525 positioned in the duodenum 515 of a patient and directed into the duct of interest (e.g., the pancreatic duct 505). A distal end of the wire guide 175 may be advanced across the treatment site (stricture) 520 and positioned distal of the obstructed region 520. The deployment system 100, which includes an outer sheath 110, the stent body 105, and the drive cable 120 connected to the cutting mechanism 115, may be advanced over the wire guide 175, through the endoscope 525, and into the duodenum 515. FIG. 7B shows a close-up view of the deployment system 100 shown in FIG. 7A. The deployment system 100 may also include a pushing catheter 180 (see FIG. 6).

During transport of the stent body 105 within the outer sheath 110, the cutting mechanism 115 is preferably positioned in an open configuration adjacent to an outer surface of the stent body 105. According to an embodiment in which the cutting mechanism is a wire 135 having a noose or snare configuration, as shown in FIG. 7B, the wire 135 may be circumferentially disposed about (looped about) the stent body in the open position. According to an embodiment in which the cutting mechanism 115 is a scissor mechanism 235, the scissor mechanism 235 may be disposed adjacent to the stent body 105 with blades 250 spread apart, as shown for example in FIG. 2. The blades 250 may partially surround the stent body 105 during delivery. Alternatively, the cutting mechanism 115 may be disposed distal of the stent body 105 in an open, partially open, or closed position during passage of the deployment system 100 through the endoscope 525 and into the duodenum 515.

After the deployment system 100 has reached the duodenum 515 and before directing the stent body 105 out of the outer sheath 110 and across the stricture 520, the cutting mechanism 115 is preferably positioned in the open configuration at the desired site of a proximal end of the stent 105a (i.e., once the stent body 105 has been cut). Generally, it is desired that the proximal end of the stent 105a protrude a short distance (e.g., about 1 cm to about 4 cm) out of the duct to facilitate drainage of fluids from the duct. The endoluminal positioning of the cutting mechanism 115 may be controlled by manipulating an actuator outside the patient's body in communication with the proximal end of the drive cable.

Figure 8A:
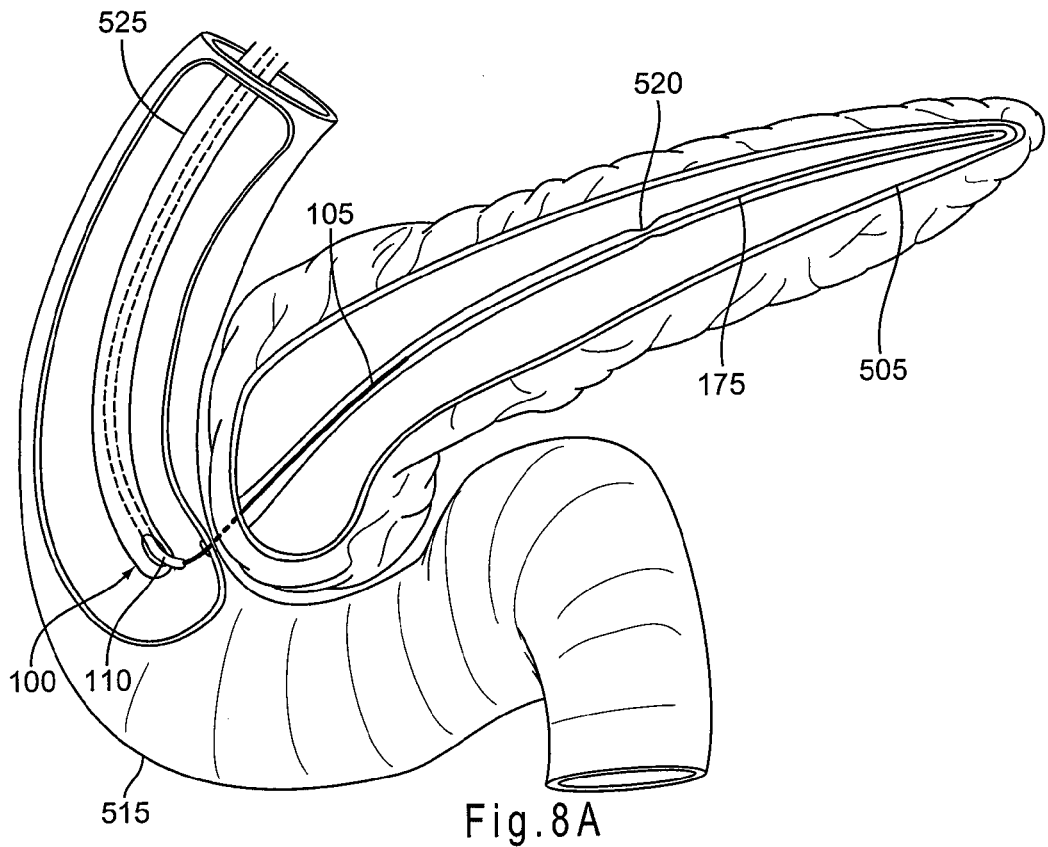
FIG. 8A is a schematic showing introduction of a stent into the pancreatic duct according to one aspect of the method.
Figure 8B:
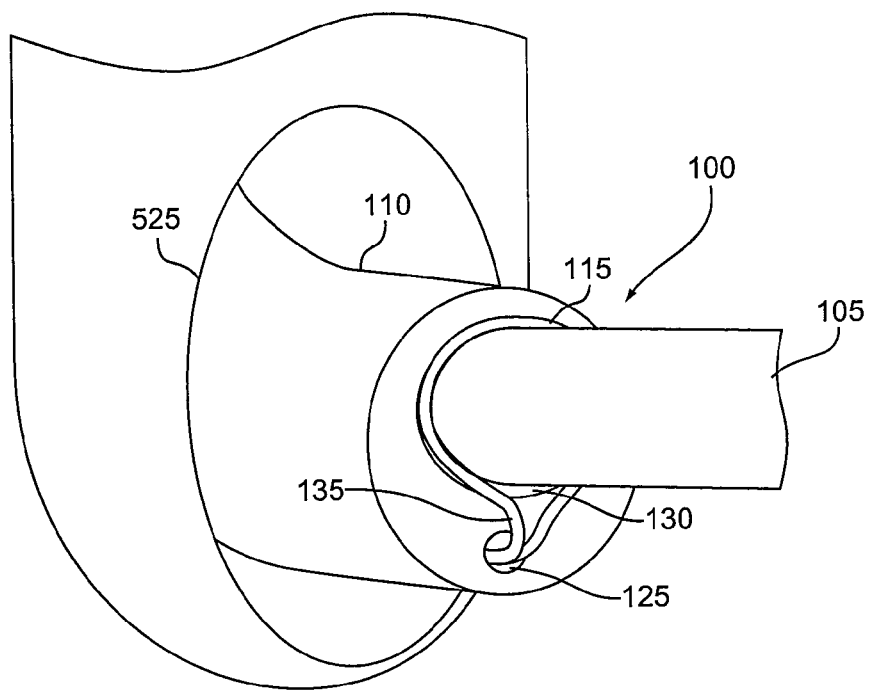
FIG. 8B is a close-up view of a portion of the deployment system used in FIG. 8A.

The stent body 105 may then be directed out of the outer sheath 110 and into the pancreatic duct 505, as shown in FIG. 8A. A distal end of the stent body 105 may be advanced across the ductal obstruction 520. According to one embodiment, the pushing catheter 180 (see FIG. 6) is employed to position the stent body 105 in the duct 505. Alternatively, the stent body 105 itself may be moved by the clinician if the length of the stent body 105 extends outside the patient. The deployment procedure is preferably performed under fluoroscopic guidance.

Figure 9:
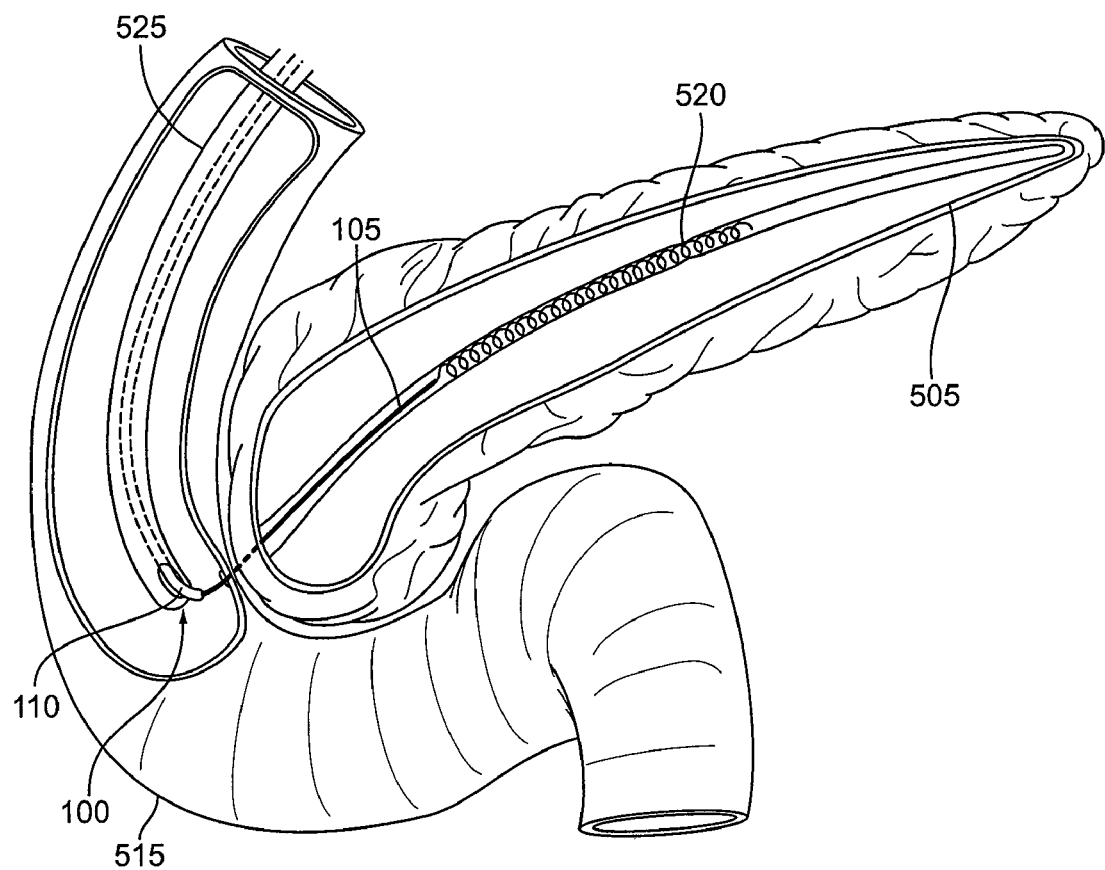
FIG. 9 is a schematic showing retraction of a wire guide from the pancreatic duct according to one aspect of the method.

As the stent body 105 comes into contact with body tissue during delivery into the duct, the temperature of the stent body 105 may increase and approach or reach body temperature. A stent body 105 formed of a shape memory polymer with a transformation temperature at or below body temperature, as described above, may transform from a straight but pliable second configuration to a coiled first configuration, for example, when it surpasses the transformation temperature. Accordingly, it may be advantageous to cool the stent body 105 during delivery to prevent premature transformation to the coiled first configuration. According to one exemplary embodiment, the wire guide 175 may be cooled by a cooling unit disposed outside the body in order to maintain the stent body 105 below the transformation temperature during delivery. It may be necessary to retract the wire guide 175, as indicated in FIG. 9, for the stent body 105 to adopt the coiled configuration in the duct. It is preferred that the wire guide 175 be retracted prior to severing the stent body 105 with the cutting mechanism 115.

Figure 10A:
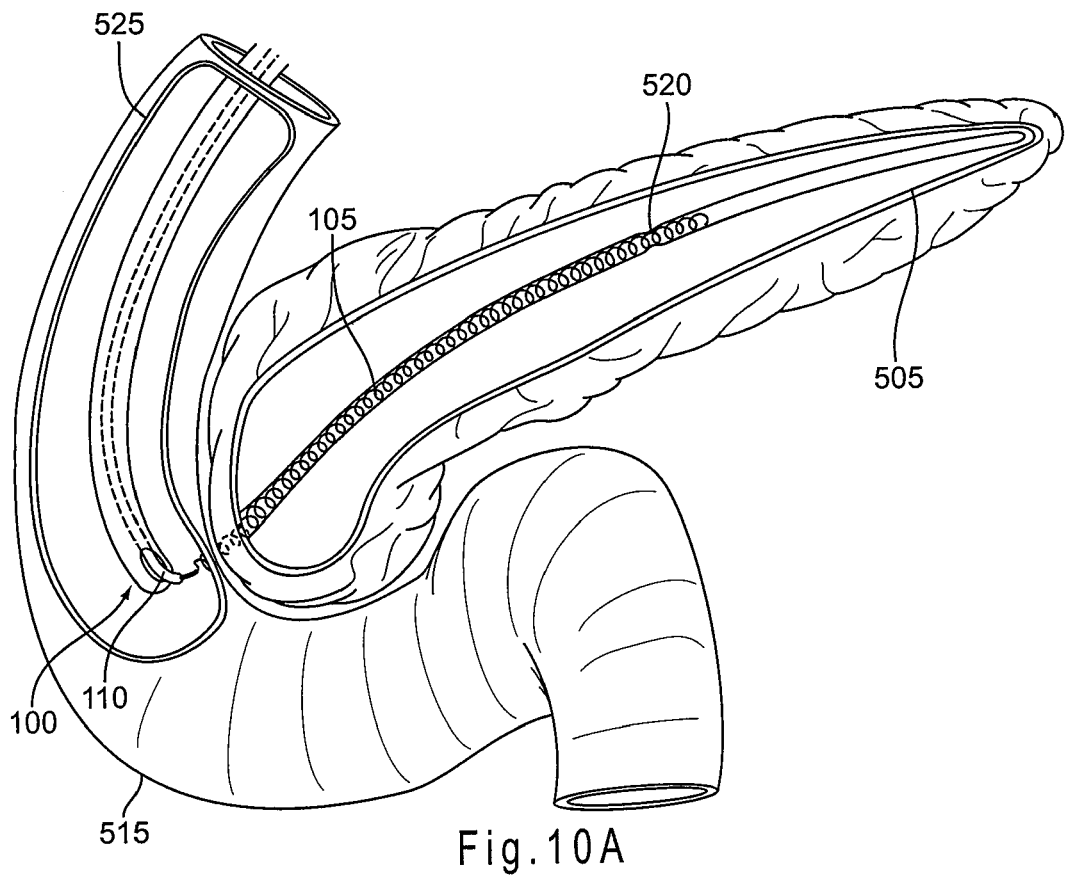
FIG. 10A is a schematic showing activation of a cutting mechanism according to one aspect of the method.
Figure 10B:
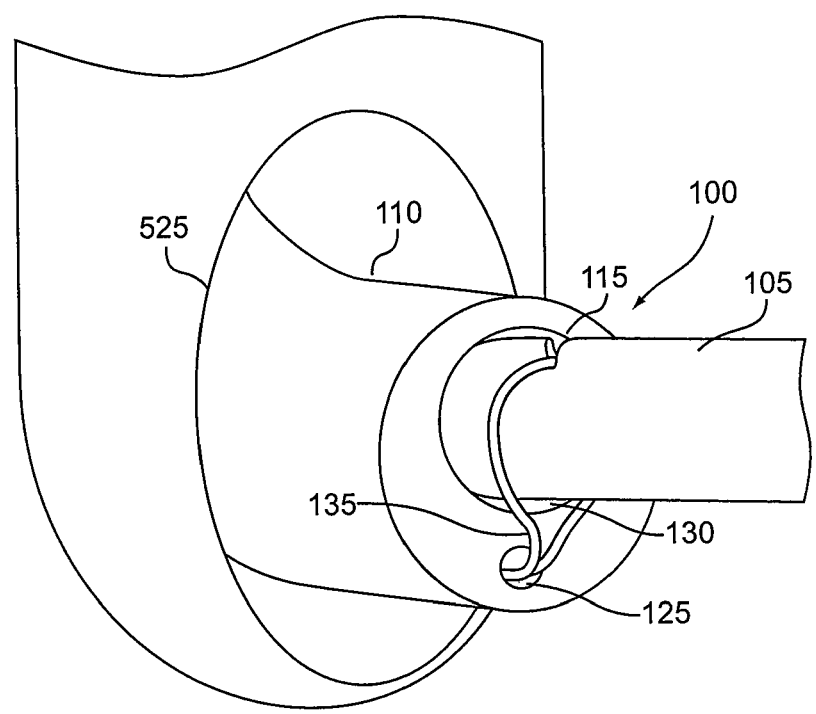
FIG. 10B is a close-up view of the deployment system used in FIG. 10A.
Figure 11:
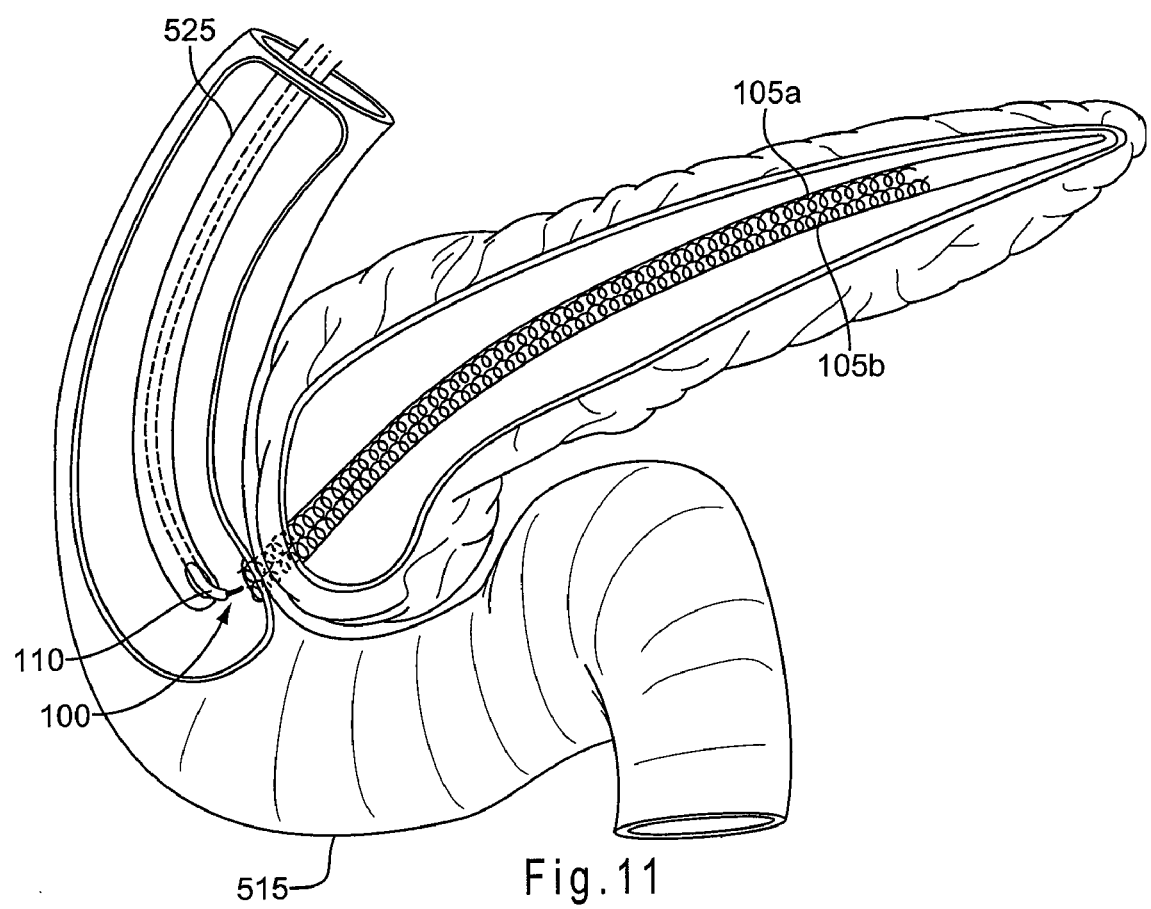
FIG. 11 is a schematic showing the deployment of more than one stent in the pancreatic duct, according to one embodiment.

Once the coiled stent body 105 is properly positioned in the duct 505, the drive cable 120 may be retracted into the secondary lumen 125 of the outer sheath 110 to close the cutting mechanism 115 about the stent body. Once again, the motion of the drive cable 120 may be controlled by manipulating the actuator outside the patient. The stent body 105 may thereby be cut to form a stent 105a of a desired length endoluminally, as shown in FIGS. 10A and 10B. Once the stent 105a has been cut to the desired length, the duct 505 may be recannulated with the wire guide 175, and the procedure may be repeated one or more times for the placement of one or more additional stents (e.g., 105b) of a desired length, as shown for example in FIG. 11.

It is also envisioned that the method may be carried out without the use of a wire guide. According to this embodiment, a stent body taking the form of a solid rod with no wire guide lumen may be delivered into the duodenum within the outer sheath 110 described above, along with the drive cable and cutting mechanism. The deployment system and the stent body, or preferably just the stent body, may then be inserted into the papilla (opening) at the base of the duct. The stent body may be used to cannulate the duct and directed across the stricture. The outer sheath and cutting mechanism may be positioned at the appropriate place in the duodenum for cutting the stent body to a stent of a desired length. According to this embodiment, there is no wire guide to retract prior to cutting the stent body. In addition, the stent body itself may be used to cannulate and recannulate the duct for the deployment of one or more stents. Because of the absence of a wire guide lumen, the stent body may have a small diameter commensurate with that of a typical wire guide, and thus may be well suited for cannulating the duct.

A single stent body may be used for the deployment of more than one stent since the stent body may be severed into a deployed portion (i.e., the stent of the desired length) and an undeployed portion that preferably remains in the outer sheath. The undeployed portion may be deployed in a subsequent severing operation. Accordingly, the stent body delivered within the outer sheath may have a length at least as long as the length of each undeployed (e.g., uncoiled) stent to be placed in the duct. An approximation of the needed length L of the stent body may be obtained using the following formula: $L = n \cdot \pi \cdot D \cdot N_t$, where n is the number of stents to be placed in the duct, D is the coil diameter of the stents, and $N_t$ is the number of turns of the coil per stent. There is no limit on the length of the stent body that may be used. If the length is such that a proximal end of the stent body extends outside the patient, then a pushing catheter may not be needed to direct the stent body, at least initially. Instead, the stent body may be advanced by pushing directly on the proximal end of the stent body. Once one or more stents have been placed in the duct of interest and the stent body has been advanced a sufficient distance distally such that the proximal end is no longer outside the patient, then a pushing catheter may be employed to advance and deploy additional stents.

A system and a method for forming at least one stent of a desired length endoluminally have been described herein. The system and method may advantageously allow a clinician to place one or more stents of customized lengths in a body vessel or duct, such as the pancreatic or bile duct. Unlike existing stent deployment methods, the method described herein does not require that the needed stent length be determined before the stent is placed into the duct. The system and method may be particularly advantageous for the placement of multiple stents in the duct of interest. In addition, the system and method may allow larger diameter ducts to be opened with fewer stents.

Although the present invention has been described in considerable detail with reference to certain embodiments thereof, other embodiments are possible without departing from the present invention. The spirit and scope of the appended claims should not be limited, therefore, to the description of the preferred embodiments contained herein. All embodiments that come within the meaning of the claims, either literally or by equivalence, are intended to be embraced therein. Furthermore, the advantages described above are not necessarily the only advantages of the invention, and it is not necessarily expected that all of the described advantages will be achieved with every embodiment of the invention.

The invention claimed is:

1. A system for forming a stent of a desired length at an endoluminal site, the system comprising:
   an elongate stent body severable into a deployed portion and an undeployed portion thereof and including a marking pattern along a length thereof, the stent body including a central lumen sized to receive a wire guide;
   an outer sheath overlying the stent body, the outer sheath including a primary lumen and a secondary lumen, the stent body being slidingly disposed within the primary lumen in a substantially straight but pliable configuration and comprising a coiled configuration at an endoluminal treatment site;
   an endoluminal cutting mechanism comprising a wire in a snare configuration operatively connected to a drive cable slidingly disposed within the secondary lumen of the outer sheath, wherein the cutting mechanism is configured to sever the stent body into the deployed portion and the undeployed portion in response to motion of the drive cable within the secondary lumen, and wherein the marking pattern comprises a regular arrangement of markers for estimating a length of each of the deployed portion and the undeployed portion of the stent body.

2. The system of claim 1, wherein the outer sheath comprises a first tubular body including the primary lumen and a second tubular body including the secondary lumen, the second tubular body being adjoined to the first tubular body.

3. The system of claim 1, wherein the drive cable has a length sufficient for the motion thereof to be actuated from outside a body lumen.

4. The system of claim 1, wherein the endoluminal cutting mechanism is configured to generate heat.

5. The system of claim 4, further comprising an electrical power source in communication with a proximal portion of the drive cable for passing a current through the cutting mechanism.

6. The system of claim 1, wherein the endoluminal cutting mechanism includes a radiopaque material.

7. The system of claim 1, wherein the stent body comprises a shape memory polymer.

8. The system of claim 1, wherein the marking pattern along the length of the stent body comprises a regular arrangement of radiopaque markers.

9. The system of claim 1, wherein the drive cable has a length sufficient for the motion thereof to be actuated from outside a body lumen,
   wherein the endoluminal cutting mechanism is configured to generate heat,
   wherein the stent body comprises a shape memory polymer, the stent body having a substantially straight but pliable configuration within the outer sheath and a coiled configuration at an endoluminal treatment site, and
   wherein the undeployed portion of the stent body is severable into a second deployed portion and a second undeployed portion.

10. A method of forming at least one stent of a desired length endoluminally, the method comprising:
    directing a deployment system into a body lumen over a wire guide, the deployment system comprising an elongate stent body having a central lumen overlying the wire guide and an outer sheath comprising a primary lumen overlying the stent body, the stent body including a marking pattern comprising a regular arrangement of markers along a length thereof, the deployment system further comprising an endoluminal cutting mechanism comprising a wire in a snare configuration operatively coupled to a drive cable slidingly disposed in a secondary lumen of the outer sheath;
    positioning the stent body at an endoluminal site;
    retracting the wire guide; and
    moving the drive cable within the secondary lumen to sever the stent body to form a stent of a desired length at the endoluminal site, an undeployed portion of the stent body remaining in the outer sheath and the stent adopting a coiled configuration at the endoluminal site.

11. The method of claim 10, wherein severing the stent body comprises passing a current through the cutting mechanism.

12. The method of claim 10, wherein positioning the stent body at an endoluminal site and severing the stent body are carried out more than one time to form more than one stent of a desired length from the stent body.

13. The method of claim 1, wherein the undeployed portion of the stent body is severable into a second deployed portion and a second undeployed portion.

* * * * *

UNITED STATES PATENT AND TRADEMARK OFFICE
CERTIFICATE OF CORRECTION

PATENT NO. : 7,691,125 B2  Page 1 of 1
APPLICATION NO. : 11/867515
DATED : April 6, 2010
INVENTOR(S) : Richard W. Ducharme It is certified that error appears in the above-identified patent and that said Letters Patent is hereby corrected as shown below:

In column 12, claim 9, lines 27-29, delete "the stent body having a substantially straight but pliable configuration within the outer sheath and a coiled configuration at an endoluminal treatment site,".

In column 12, claim 11, line 54, after "current through the" replace "cuffing" with --cutting--.

Signed and Sealed this

Seventeenth Day of August, 2010

David J. Kappos
*Director of the United States Patent and Trademark Office*